(12) United States Patent
Brotzge et al.

(10) Patent No.: US 10,182,891 B2
(45) Date of Patent: Jan. 22, 2019

(54) DENTAL DEVICE

(71) Applicant: Ivoclar Vivadent AG, Schaan (LI)

(72) Inventors: Michael Brotzge, Koblach (AT);
Johannes Lorünser, Bludenz (AT);
Robert Grünenfelder, Eschen (CH);
Philipp Kettner, Rankweil (AT)

(73) Assignee: Ivoclar Vivadent AG, Schaan (LI)

( * ) Notice: Subject to any disclaimer, the term of this patent is extended or adjusted under 35 U.S.C. 154(b) by 167 days.

(21) Appl. No.: 14/127,609

(22) PCT Filed: Jan. 24, 2013

(86) PCT No.: PCT/EP2013/051272
§ 371 (c)(1),
(2) Date: Dec. 19, 2013

(87) PCT Pub. No.: WO2013/110678
PCT Pub. Date: Aug. 1, 2013

(65) Prior Publication Data
US 2014/0336805 A1     Nov. 13, 2014

(30) Foreign Application Priority Data

Jan. 27, 2012   (EP) .................................... 12152931

(51) Int. Cl.
*G05B 13/02*       (2006.01)
*A61C 13/00*       (2006.01)
(Continued)

(52) U.S. Cl.
CPC .......... *A61C 13/0004* (2013.01); *A61C 9/004* (2013.01); *A61C 19/003* (2013.01);
(Continued)

(58) Field of Classification Search
CPC . A61C 13/20; A61C 13/0004; A61C 13/0006; A61C 13/00; Y10T 29/49567; F27B 17/025; F27B 5/18
See application file for complete search history.

(56) References Cited

U.S. PATENT DOCUMENTS 5,072,360 A    12/1991  Knorpp et al.
5,372,502 A    12/1994  Massen et al.
(Continued)

FOREIGN PATENT DOCUMENTS

CN      100998522 A      7/2007
DE      19510685 A1     10/1996
(Continued)

OTHER PUBLICATIONS

Lain et al., WO-1999017250-A1.*
(Continued)

*Primary Examiner* — Darrin D Dunn
(74) *Attorney, Agent, or Firm* — Ann M. Knab; Thad McMurray

(57) ABSTRACT

The invention relates to a dentel device for the treatment of a dental restoration part, comprising at least one operating program, a storage of the dental device and at least one detection device for at least one object. The detection device can detect data of the object and this data, in particular together with an operating program associated with the object, can be stored in a storage of the dental device or can be compared to the data of objects which have been stored in advance in the storage of the dental device. The dental device, depending on the comparison result of the data of a detected object with the data of objects which have been stored in advance in the storage of the dental device, starts the associated operating program or shows it for selection.

15 Claims, 3 Drawing Sheets

(51) Int. Cl.
  *A61C 9/00* (2006.01)
  *A61C 13/15* (2006.01)
  *F27B 17/02* (2006.01)
  *F27D 19/00* (2006.01)
  *F27D 21/00* (2006.01)
  *A61C 13/20* (2006.01)

(52) U.S. Cl.
  CPC ............ *F27B 17/025* (2013.01); *F27D 19/00* (2013.01); *F27D 21/00* (2013.01); *A61C 13/20* (2013.01)

(56) References Cited

U.S. PATENT DOCUMENTS

| | | | | |
|---|---|---|---|---|
| 6,229,922 B1* | 5/2001 | Sasakawa | | G06F 7/02 |
| | | | | 382/209 |
| 6,287,121 B1 | 9/2001 | Guiot et al. | | |
| 6,358,047 B2* | 3/2002 | Lehmann | | A61C 19/10 |
| | | | | 356/408 |
| 6,519,607 B1* | 2/2003 | Mahoney | | G06F 3/017 |
| | | | | 707/769 |
| 6,864,229 B2 | 3/2005 | Kuliopulos et al. | | |
| 7,108,508 B2 | 9/2006 | Hedge et al. | | |
| 7,454,775 B1* | 11/2008 | Schaffer | | H04N 7/16 |
| | | | | 348/E7.054 |
| 7,599,527 B2* | 10/2009 | Shah | | G06K 9/03 |
| | | | | 382/118 |
| 7,623,942 B2 | 11/2009 | Touchstone | | |
| 7,656,402 B2* | 2/2010 | Abraham | | G06Q 30/06 |
| | | | | 345/419 |
| 7,995,195 B2 | 8/2011 | Feichtinger et al. | | |
| 8,311,294 B2* | 11/2012 | Myers | | G06K 9/00288 |
| | | | | 382/118 |
| 8,452,614 B2 | 5/2013 | Nyholm | | |
| 8,684,229 B2 | 4/2014 | Harre | | |
| 2001/0038705 A1 | 11/2001 | Rubbert et al. | | |
| 2003/0010536 A1 | 1/2003 | Swartz | | |
| 2003/0101526 A1 | 6/2003 | Hischer | | |
| 2003/0225777 A1* | 12/2003 | Marsh | | H04N 7/163 |
| 2004/0252303 A1* | 12/2004 | Giorgianni | | G01J 3/508 |
| | | | | 356/402 |
| 2005/0175949 A1* | 8/2005 | Grunenfelder | | A61C 13/20 |
| | | | | 432/120 |
| 2005/0244975 A1 | 11/2005 | Rakow et al. | | |
| 2006/0257816 A1* | 11/2006 | Klemola | | A61B 6/4233 |
| | | | | 433/29 |
| 2007/0039023 A1* | 2/2007 | Kataoka | | H04N 5/44543 |
| | | | | 725/46 |
| 2008/0237211 A1 | 10/2008 | Jussel | | |
| 2008/0250479 A1* | 10/2008 | Matoba | | G06F 3/1204 |
| | | | | 726/5 |
| 2008/0256579 A1* | 10/2008 | Verhaegh | | H04N 5/44513 |
| | | | | 725/46 |
| 2009/0087818 A1 | 4/2009 | O'Brien et al. | | |
| 2009/0106314 A1* | 4/2009 | Song | | G06K 9/6272 |
| 2009/0113335 A1* | 4/2009 | Sandoe | | G06F 19/3406 |
| | | | | 715/773 |
| 2009/0117504 A1 | 5/2009 | Grunenfelder | | |
| 2009/0228424 A1* | 9/2009 | Mori | | H04H 60/31 |
| | | | | 706/54 |
| 2010/0030365 A1* | 2/2010 | Lilly | | B23Q 17/20 |
| | | | | 700/163 |
| 2010/0047731 A1 | 2/2010 | Zubler | | |
| 2010/0107108 A1* | 4/2010 | Husoy | | G06F 9/4443 |
| | | | | 715/777 |
| 2010/0303315 A1* | 12/2010 | Rohner | | G01J 3/02 |
| | | | | 382/128 |
| 2011/0153034 A1* | 6/2011 | Philliben | | G05B 23/0216 |
| | | | | 700/17 |
| 2011/0188086 A1* | 8/2011 | Lehmann | | A61C 19/10 |
| | | | | 358/1.18 |
| 2011/0200966 A1 | 8/2011 | Heinz et al. | | |
| 2011/0229840 A1 | 9/2011 | Liang et al. | | |
| 2011/0247036 A1* | 10/2011 | Adimatyam | | H04N 5/44543 |
| | | | | 725/40 |
| 2011/0269097 A1* | 11/2011 | Sporbert | | A61C 7/00 |
| | | | | 433/24 |
| 2012/0100508 A1* | 4/2012 | Lehmann | | C07K 14/705 |
| | | | | 433/223 |
| 2012/0167127 A1* | 6/2012 | Uchida | | H04N 21/4223 |
| | | | | 725/14 |
| 2012/0310386 A1* | 12/2012 | To | | G05B 15/02 |
| | | | | 700/83 |
| 2013/0026157 A1 | 1/2013 | Jussel | | |
| 2013/0029280 A1 | 1/2013 | Jussel | | |
| 2013/0029281 A1 | 1/2013 | Jussel et al. | | |
| 2013/0083999 A1* | 4/2013 | Bhardwaj | | G06Q 30/0643 |
| | | | | 382/165 |
| 2013/0125002 A1* | 5/2013 | Spaeth | | G06F 3/0482 |
| | | | | 715/731 |
| 2015/0010876 A1 | 1/2015 | Grunenfelder et al. | | |
| 2015/0265381 A1* | 9/2015 | Fisker | | A61C 13/0004 |
| | | | | 703/1 |

FOREIGN PATENT DOCUMENTS

| | | |
|---|---|---|
| DE | 102004026107 A1 | 12/2005 |
| JP | H05270209 A | 10/1993 |
| JP | A1993290209 A | 11/1993 |
| JP | 1999216150 A | 7/1999 |
| JP | 2004272357 A | 9/2004 |
| RU | 2439489 C1 | 1/2012 |

OTHER PUBLICATIONS

Ivoclar Vivadent, "EP 600 Combi Press Furnace and Ceramic Furnace Operation Manual", Version 4, Issued Jun. 2005.
Eichner, K. et al, "Dental Materials and Their Processing; vol. 1: Basics and Processing," Hüthig GmbH, Heidelberg, pp. 341, 1996.
Hohmann/Helscher, "Lexicon of Dental Technology," Verlag Neuer Merkur GmbH, Munuch, pp. 103, 1998.

* cited by examiner

DENTAL DEVICE

CROSS-REFERENCE TO RELATED APPLICATIONS

This application is a National Stage application of International patent application PCT/EP2013/051272 filed on Jan. 24, 2013, which claims priority to European patent application No. 12152931.7 filed on Jan. 27, 2012, the disclosures of which are incorporated herein by reference in their entirety.

The invention relates to a dental device for the treatment of a dental restoration part, according to the preamble of claim 1.

It has been known for long to operate dental devices such as dental furnaces, but also light curing devices, in a program-controlled way. One of the numerous examples hereof is DE 38 31 539 A1; in this solution, different parameters can be set, as desired by the user.

DE 199 13 891 A1 discloses a control method for a dental device in which a firing cycle is to be realized in a program-controlled and material-dependent way. The movement of a piston is detected and shutdown is started depending on the movement profile.

The detection of the temperature of furnaces has been known for a long time, as is the control of furnaces based on the measuring result. Examples hereof are DE 10 2007 035 609 A1 and EP 2 105 691 A1.

Furthermore, it has come to be known to use a camera for the detection of the oral situation of a patient in order to then also control a CAD/CAM device for the provision of the dentures, if necessary.

Such solutions have become known in numerous modifications and attempts have been made for a long time to provide a restoration result which is as optically appealing as possible by visually comparing a denture to be produced with the neighboring teeth and by selecting the corresponding tooth color.

In this connection it has been suggested to detect the tooth color and further parameters of the neighboring teeth, to evaluate them electronically and to select the tooth color of a tooth key which is closest to the evaluation for producing the dental restoration.

Furthermore, it has also been suggested to visualize such replacement teeth and to display them electronically, to - similar to the "virtual hairstyle"—gain an impression, in advance, of the aesthetics of the restoration result to be produced.

However, the solutions known are provided with deficiencies.

Therefore, it is the task of the invention to create a dental device according to the preamble of claim 1 which is significantly improved in terms of operability without any reductions in the quality of the dental restoration parts to be produced.

This task is inventively solved by claim 1. Advantageous develeopments may be taken from the subclaims.

According to the invention it is expecially favorable that the dental device can give the correct reaction quasi automatically when the detection device detects the object, for instance to start a corresponding program or to show it for selection. This happens preferably via an image recognition which processes the image taken by a camera of the detection device and quasi identifies the object upon the presence of characteristic features.

Identification happens by means of a sort of database which contains a plurality of given reference objects and which has already been produced in advance and which is stored in the dental device and/or a server and/or on the internet (cloud). When a certain number of features of a reference object corresponds to the image of the object detected, the release takes place, for instance, the corresponding operating program is started.

According to the invention an improvement of the restoration capability can be combined with a better adaptability to different restoration situations, taking into consideration the complex control of dental devices, in particular of light curing devices, but also of furnaces.

Even if the dental technician operating the device, or maybe even the dentist, has to meet sophisticated requirements, he or she can inventively make the entries demanded by the dental device as he or she is supported by the dental device.

According to the invention the number of possible parameters can be reduced when operating the dental device; in the base setting only few setting possibilites have to be maintained which will then cover the most frequent operating versions.

This inventively prevents the dental technician from being overstrained when he or she has to handle a less common operating situation because, according to the invention, he or she is not only trained for the base settings of the dental device but carries out the detailed operation which is necessary for less common treatment situations.

In this way high-quality dental restoration results can be achieved taking into account a special adjustment of the necessary parameters of the dental device to produce the dental restoration parts, even when adjusting to each respective individual case.

According to a particularly preferred embodiment of the invention it is provided to gradually determine the matching according to the features. If, for instance, a match is determined above a first threshold value, a number of reference objects is displayed to the user for selection. The user can then choose the desired reference object or the respective operating program.

If the match exceeds a second threshold value and/or if only one matching reference object remains, the operating program can be executed automatically or can be started or displayed for selection.

As an example, a data base has stored 15 features—corresponding to 15 data fields—per reference object. The first threshold value is e.g. set to 11 features, the second to 13.

If the comparison device then determines by means of the image recognition system that there is a match between the object detected and several reference objects in 13 (or more) features, these features are displayed to the user of the dental device, for instance by an attached display device. The data base is provided with 5 entries for which there is a match in 11 features and the user can then, for instance by touching the touch screen of the display device, choose the respective operating program. Here, the respective operating program can preferably be identified itself, in addition, and is located adjacent to the respective reference object on the screen of the display device.

In a second case of the same dental device, it is pretended that the object matches with one of the reference objects in 13 features which are stored in the data base.

This reference object is then selected almost automatically and the associated operating program stored in the dental device is executed either immediately or upon confirmation by the user.

If, as an alternative, there is a match with 2 reference objects, they are offered for selection in spite of having reached a second threshold value on the display device, and the user has to decide for one of the operating programs.

A further case is the opportunity of pre-selection: The user chooses in advance, i.e. before the object can be detected by the detection device, which type of operating program comes into question. The type of operating program can also be understood as numerous operating programs combined into one group each.

When the dental device is formed as a dental furnace, e.g., the operating program group "Sintering" can be differentiated from the operating program group "Glaze Firing".

In this case, the user pre-selects the operating program group "Sintering".

Analagous to the latter case, it is pretended that one of the reference objects belongs to the operating program group "Glaze Firing" and one to the operating program group "Sintering".

As the operating program group "Glaze Firing" has been excluded in advance by pre-selection, with 13 determined matching features only the reference object from the operating program group "Sintering" remains so that the assignment is unique and the associated operating program can be started automatically without the user having to make an additional selection.

In accordance with the invention it is especially favorable that the inventive dental device can be operated easily but still facilitates a high-quality individual treatment adjusted to the respective object.

Here, the object can correspond to the dental restoration part or its intermediate product but does not have to. In one possible embodiment the object is the face or fingerprint of a user. In a further embodiment the object is the non-fired dental bridge, the non-fired individual tooth or the non-fired crown.

In a further embodiment the object is a muffle which has been prepared for firing and pressing in a muffle furnace, but is provided in an unprocessed state.

In a further embodiment the object is a material and adjustment is carried out by the selection of the operating programs or operating program groups which are suitable for that material.

It is important that the object is assigned to the selected program or the selected program group and is stored as a reference object together with the program or the program group.

The detection device can be provided with a camera and the object can then be preferably held in front of the camera. A display device of the furnace then displays the object in the detected form. Via the image recognition device which is typically realized in the form of a software an object which has the same or a similar shape will then be displayed for selection or immediately selected wherein starting the operating program may either be carried out automatically or by pressing a confirmation button by the user.

If no object with the same shape is stored, the objects which are most similar are being displayed by the display device and offered to the user for selection.

It is to be understood that different objects when detected in a two-dimensional way result in different images, depending on their orientation in space. This means, however, that the images detected by the detection device are different, depending on the orientation of the object. In order to still facilitate a reliable recognition there is either the possibility of carrying out a three-dimensional detection. For this purpose, for instance, 3 cameras of the detection device can be directed at the object from different and suitably chosen solid angles, and detection and thus image recognition will be carried out in a three-dimensional way.

A further possibility is to specify the desired solid angle to the user.

A third possibility when detecting in a two-dimensional manner is to generally require the view of the longest side so that the respective camera is always directed at the "broadside" of the object.

In this solution the user is suitably asked to turn the object, and when the desired orientation which corresponds to the longest side of the object in two-dimensional scanning is detected, this image is used as a basis of comparison.

It is to be understood that the camera of the detection device can have a detection range within and beyond the dental device. For instance, in a furnace it can be detected how many teeth have been introduced into the firing chamber and how large they are, before the firing starts. The firing parameters can then be set depending on the mass of the dental restoration parts which has been deduced by their size.

In an advantageous embodiment it is also possible to have the dental device execute an additional function when recognizing the object prior to the end of the acutal operating program. Here it is, for instance, possible to automatically open the furnace hood after the evaluation of the comparison result and thus after the determination of the necessary operating program for a dental restoration part which is located close to a dental furnace and to ask the user to place the dental restoration part(s) onto the bottom of the furnace in the firing chamber, in order to immediately lower the firing hood and make the furnace start, after having placed the part(s) into the furnace.

As two detection steps are desirable in this case, it is preferred to either work with two cameras or to detect, using a mirror or another device to deflect radiation, which dental restoration part is held close to the dental furnace and on the other hand to detect if the respective dental restoration part is located in the firing chamber.

For recognizing the dental restoration part it is favorable if physical parameters of the object are chosen. Among them are the size, the contour in the two-dimensional view, the color of the object, its surface condition and further parameters of the object which can be detected by the detection device.

It is also possible to use a two-step process for objects which cannot be identified precisely. The operating programs of the dental device are expediently summarized into operating program groups. When detecting an object a selection of possible operating programs is displayed at a relatively clear determination and at a low level of correlation of features a selection of possible operating program groups is shown first. As soon as the user selects the desired operating program group, the available operating programs within this group suitable for the object are displayed.

It is to be understood that it has to be taken care of the event that no operating program fits the object detected. In case of non-matches or at least non-similarities of the object with one of the reference objects, i.e. when determining that not even one of the reference objects from the data base of the dental device is similar to the object detected, no operating program and no operating program group is explicitly suggested to the user. The operating programs are being locked and/or the user is asked to use another object.

If the dental device is designed in such a way that when there is a unique identification of an object, i.e. a perfect correlation with the reference object and thus the determination which operating program is to be used, whose use needs to be confirmed by the user, besides the possibility of using a button as a confirmation indicator, there is also the possibility that the user makes a confirmation gesture which is in turn detected by the camera of the detection device and is understood as a confirmation indicator by the dental device so that the respective operating program is started.

The data base containing the reference objects can be stored locally in the dental device. However, there is also the possibility of storing the data base on a central server and of maintaining it whereas it is to be understood that a respective connection to the data base is necessary in that case in order to facilitate access to the data base.

There is also the possibility of storing a local copy of the server data base in the dental device which will then be updated automatically by the server data base upon existence of, e.g., an internet connection.

The display device of the dental device can either be connected to it or incorporated into the furnace. It is also possible, for instance in a furnace park with a plurality of furnaces, to realize a central daughter or subsidiary display or a display switchover in a monitoring room for several furnaces.

The image recognition device is preferably suited to recognize an image of the object sent by the detection device in view of certain features and to identify the object according to these features and in this way assign it to a previously stored object.

In an advantageous development of the inventive dental device the data detected by the detection device are comparable to the data of objects previously stored in the storage unit of the dental device (10) and that the dental device, depending on the comparison result of the data of a detected object with data of objects which have been stored in advance in the storage of the dental device, starts the associated operating program or shows it for selection.

In an advantageous development of the inventive dental device it is provided that the operating program is formed by an operating program executable in the dental device (10) or by an operating program group executable in the dental device.

In an advantageous development of the inventive dental device the detection device (18) is provided with an image recognition device which is suitable for recognizing an image of the object (24) detected by the detection device and/or features of the image.

In an advantageous development of the inventive dental device the data consists of at least one image and/or at least one parameter of the object (24).

In an advantageous development of the inventive dental device the at least one parameter of the object (24) is a physical and/or optical feature of the object (24), such as the outer contour and/or the height and/or the width and/or the surface condition of the object, and/or colors and/or patterns and/or the primer coat of the object.

In an advantageous development of the inventive dental device the object (24) is a one- or multi-unit dental restoration part and/or a blank to be treated in the dental device (10) and/or a muffle and/or a packaging for a dental material which can be encoded in terms of color or symbols.

In an advantageous development of the inventive dental device the object (24) involves parts of the user, parts of his/her face, his/her hand or an identification feature used only by him/her such as his/her chip card.

In an advantageous development of the inventive dental device the detection device (18) is provided with at least one camera (20) or at least one sensor, in particular an image sensor, whose detection areas (22) extend into the interior of the dental device (10) and/or outside the dental device (10).

In an advantageous development of the inventive dental device the detection device (18) detects the position and/or the rotational position of the object (24) in space and can be pivoted in particular at the dental device (10) or relative to the dental device.

In an advantageous development of the inventive dental device comparing the data of a detected object (24) with the data of the stored objects is realized using a comparison device.

In an advantageous development of the inventive dental device if no unambiguous assignment to an operating program or an operating program group can be made when comparing the data of the detected object (24) with the stored data, the data of at least two objects (24) is displayed on a display device (14), whose data is most similar to the data of the detected object (24) and that the user himself/herself chooses the data which corresponds to the operating program or operating program group desired by him/her.

In an advantageous development of the inventive dental device the image recognition device is suitable for identifying an object (24) with the help of the detected features of an image and for starting the operating program associated with the object or for showing it for selection.

In an advantageous development of the inventive dental device the display device (14) is suitable for displaying the object (24) detected by the detection device (18) reduced or increased in size.

In an advantageous development of the inventive dental device the dental device (10) is formed by a dental furnace, or by a dental press furnace or by a light curing device.

Further details, advantages and features may be taken from the following description of the embodiments of the invention on the basis of the drawings.

Figure 1:
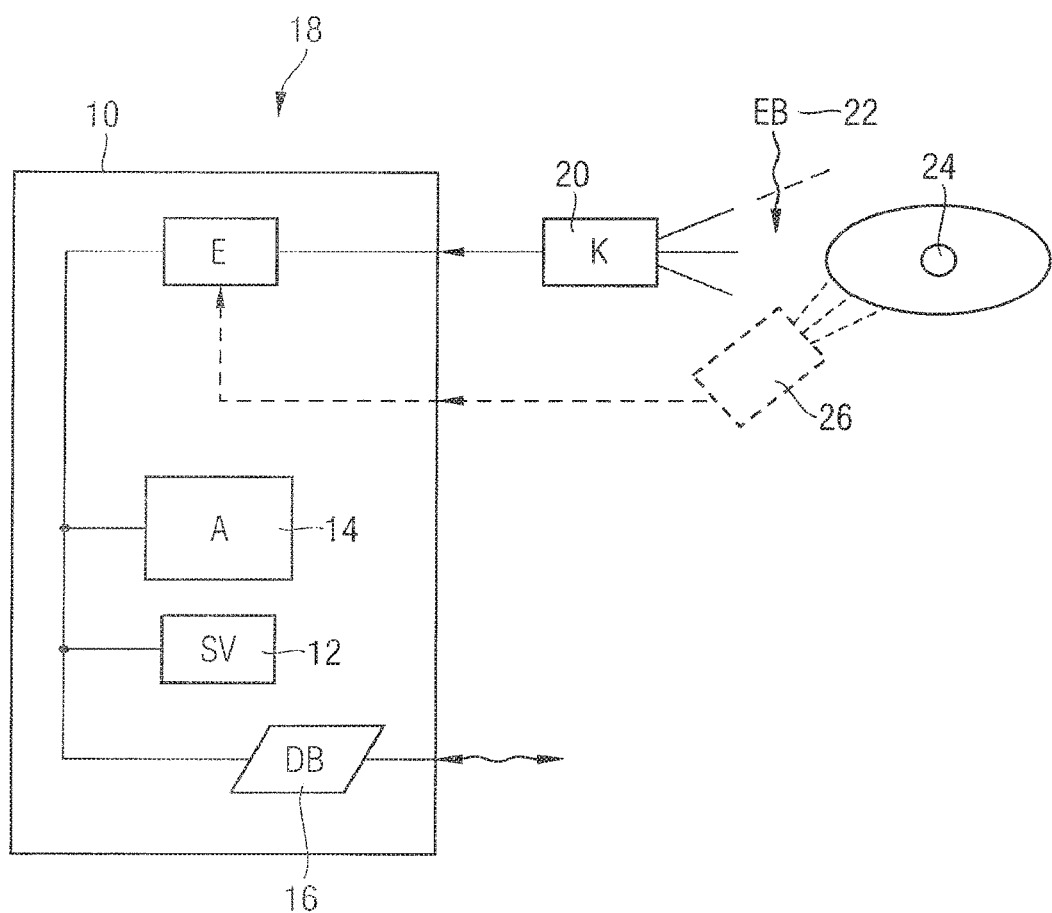
FIG. 1 shows a schematic view of an inventive dental device in one embodiment.

The dental device 10 shown in FIG. 1 is, for instance, formed as a light curing device, or preferably as a dental furnace or press furnace.

The dental device is controlled by a control device 12 which is provided with control elements not illustrated which can also be used to, e.g., select an operating program stored in the control device.

The dental device is further provided with a display device 14 which is attached to the dental furnace in the embodiment illustrated. In case the display device comprises a touchscreen, the control elements of the control device can be attached to it or displayed by it.

The control device 12 is further connected to a data base 16 which stores so-called reference objects. This is a collection of data regarding objects which are classified according to pre-determined parameters and stored similar to a data base.

The reference objects which are stored in the data base 16 are compared by the control device 12, which is insofar provided with a comparison device, with an object detected by a detection device 18. For this purpose the detection device comprises a camera 20. The camera 20, in turn, comprises a detection range 22 in which an object 24 is recorded as an image if it is located there. The detection device 18 or the control device 12 are provided with the possibility of an image recognition which evaluates the present image according to certain parameters and subsequently provides these parameters as a basis for comparison.

Among the parameters of the object are physical and/or optical properties of the object, such as the outer contour, the height and/or width of the object, or, for instance, its surface condition, its colors and/or patterns or e.g. a primer coat of the object.

This applies if the object is a dental restoration part, a muffle or similar. If the object is the face of a user, the image recognition is realized conveniently using a face recognition software known per se.

If the object is a packaging for a dental material, the recognition, for the purposes of detection, is realized conveniently using a suitable device for decoding; in the case of a bar code encoding using a bar code detection sofware.

The insofar evaluated data of the object 24 are then supplied to the comparison device in the control device 12, stored in the storage unit, if necessary, and are compared to all possible reference objects from the data base 16.

Furthermore, the operating programs of the dental device 10 are stored in the storage unit of the control device 12.

Comparison is realized via the determination of matching features and if—in the easiest case—only one of the reference objects complies with all the features of the object detected, the display device 14 shows the operating program associated with or assigned to the reference object. The operating program is then started automatically or upon confirmation by the user.

Preferably, the detected image of the object 24 is displayed by the display device 14 in order to make a visual confirmation.

In a two-dimensional detection of the object, as illustrated in FIG. 1 by solid lines, the position and/or rotary orientation of the object in space is also detected conveniently. This can, e.g., be carried out in a so-called pre-examination which decides first via the image recognition which position the object has in space. The display device 14 can then give information to the user of how to turn the object in order to facilitate recognition.

Figure 3:
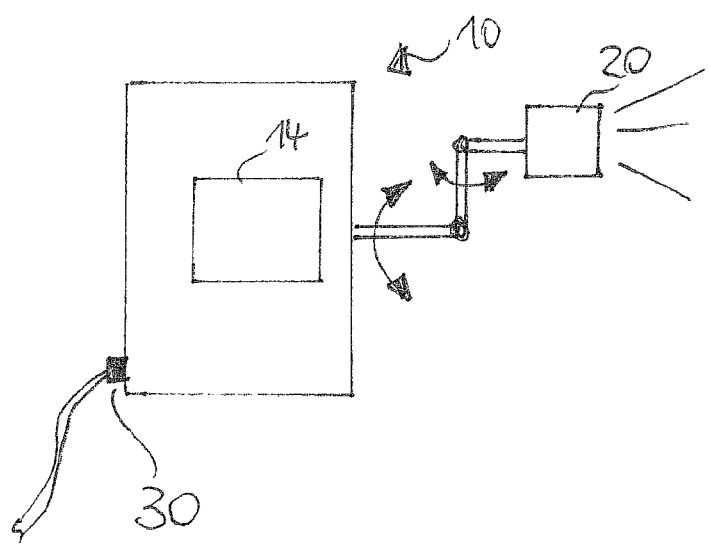
FIG. 3 shows a schematic view of a further embodiment of the inventive dental device.

It is also possible, as illustrated in FIG. 3, to attach the camera 20 of the detection device 18 to the dental device in a pivot-mounted way in order to facilitate a tracking of the object.

In the modified embodiment of the inventive dental device illustrated as dotted lines the detection device 18 is provided with a further camera 26 which is directed at an angle relative to the camera 20 askew at the object 24, and, in addition, a third camera, which is not illustrated here but is located beyond the drawing plane, preferably significantly spaced apart from it, is also directed at the object 24.

A threefold camera arrangement facilitates a three-dimensional image recognition.

It is to be understood that the type of image recognition and the way in which the reference objects are stored in the data base 16 are adjusted to the respective design of the dental device 10. While a three-dimensional image recognition facilitates a unique identification and recognition, it can be favorable to store several reference objects for each operating program group in order to make possible an adjustment to different recognitional situations of the object 24.

Figure 2:
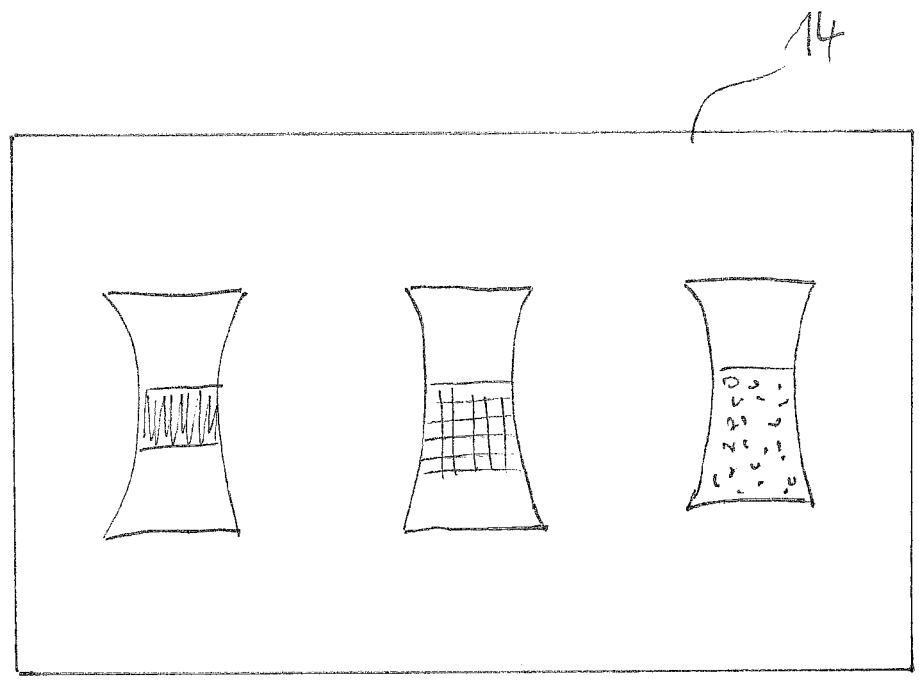
FIG. 2 shows the display of the dental device according to FIG. 1.

In a modified embodiment of the display device according to FIG. 2 not only the reference object which is recognized as being selected is displayed by the display device 14 but those reference objects which are similar to the object 24 known. In this way, the user has the chance of selecting the operating program to be started themselves to a certain extent. On the other hand, only those operating programs suitable for the object are offered to the user so that incorrect operations are virtually eliminated, and e.g. dental material or the size of a dental restoration cannot cause an inappropriate operating program, for instance at too high temperatures, to be executed. The display device 14 is formed as a touch screen in the embodiment illustrated which facilitates the selection of the respective operating program directly by touching the desired reference object 19 on the display device 14.

In so far, the inventive dental device does not only offer a substantially simplified operation but also, in particular, a significant increase in operational safety and also an improved adjustment to the individual firing parameters tailored to the respective object.

In FIG. 3 a further preferred embodiment of the inventive dental device 10 is illustrated in which the camera 20 of the detection device 18 is pivot-mounted via the joint 21 (here illustrated in two axes of rotation) at the dental device 10. It is to be understood that the camera 20 can be movably mounted in any desired other way, too, and at any desired degree of freedom in movement. Hereby, the control device 12 of the dental device 10 can control the positioning of the camera 20 in space, relative to the object 24 to be detected.

The pivoted mounting of the camera 20, for instance, makes also possible to detect the position or orientation of the object 24 to be detected in space relative to the dental device 10. For instance, a correction of the detected image of the object 24 is also made possible in order to adapt the detection angle of the object 24 to that of the stored reference object which can improve the accuracy of the comparison of desired features (contours, barcodes etc.).

The embodiment of the dental device 10 illustrated in FIG. 3 is provided with an internet connection 30 with the help of which reference objects which are not located in the own storage unit of the dental device 10 can also be used for comparison by the comparison device 28. In FIG. 2, the connection to the internet is preferably illustrated as a cable connection. It is to be understood that the connection with the internet (or with any other suitable data source such as a server, an intranet or similar) can also be made in any other desired way.

It is also to be understood that not only further reference objects but also parameters or operating programs which are adjusted to the dental device for the respective reference objects can be requested via this internet connection and that e.g. a remote surveillance of the dental device 10 is also possible via the internet connection as data can be transferred via the internet connection to the dental device 10 as well as from that device, i.e. in a bi-directional way.

Figure 4:
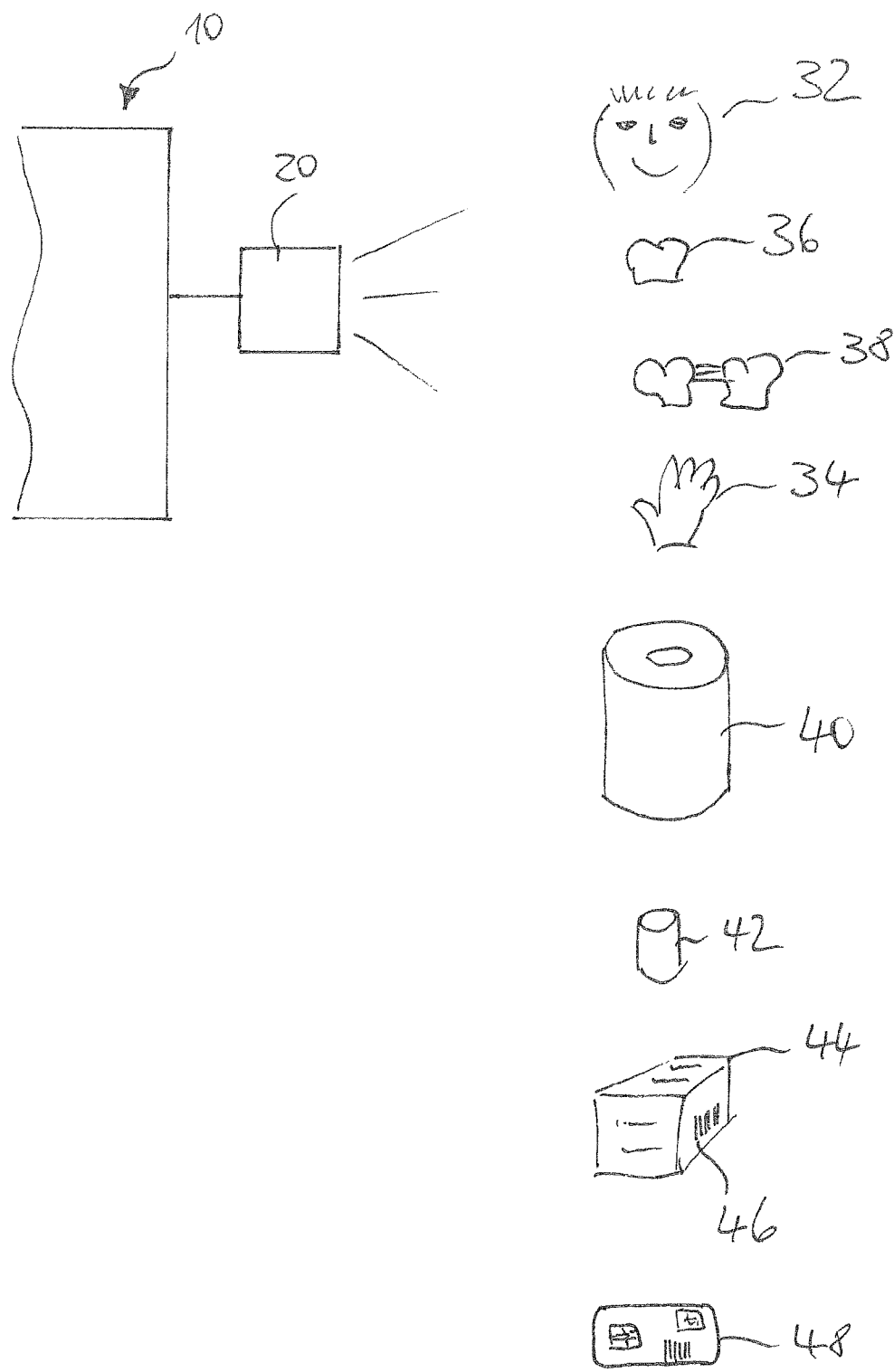
FIG. 4 shows a partial view of the inventive dental device and several possible objects which can be detected by the device.

FIG. 4 illustrates as an example several possible objects which can be detected by the camera 20 of the detection device 18. The face 32 of the user or part of it, a hand 34 or the fingerprint of the user can be detected by the inventive detection device, as well as a one-unit 36 or multi-unit 38 dental restoration part, a muffle 40, a blank 42 or the packaging 44 of a dental material to be processed.

It is to be understood that the packaging can be recognized by means of its specific properties such as color or imprint as well as by means of an available barcode 46 or similar machine-readable encodings. Furthermore, for instance, a chipcard 48 which can only be used by the user can be detected and processed for identification.

The invention claimed is:

1. Dental device for treatment of a dental restoration part by curing, firing or pressing, comprising
    at least one operating program for operating a curing light or a sintering or pressing furnace,
    a storage comprising a plurality of features and
    at least one detection device for at least one dental restoration part,
    wherein the detection device (18) can detect data of the at least one dental restoration part and the detected data, together with an operating program associated with the object, can be stored in the storage of the dental device (10),
    wherein the data detected by the detection device is compared to threshold values comprising at least a first threshold value having a first subset of features and a second threshold value having a second subset of features,
    wherein if a comparison result is greater than the first threshold value but less than the second threshold value, then an associated operating program is shown for selection and/or started,
    wherein selection of an associated operating program comprises selecting a curing program for curing one or more dental restoration parts, selecting a firing program for firing one or more dental restoration parts or selecting a pressing program for pressing one or more dental restoration parts,
    wherein starting of an associated operating program comprises one of starting a firing cycle for one or more dental restoration parts, starting a pressing cycle for one or more dental restoration parts and starting a curing cycle for one or more dental restoration parts, and
    wherein if the comparison result is greater than the second threshold value, an associated operating program is started comprising one of starting a firing cycle for one or more dental restoration parts, starting a pressing cycle for one or more dental restoration parts and starting a curing cycle for one or more dental restoration parts.

2. Dental device according to claim 1, wherein the operating program is formed by an operating program executable in the dental device (10) or by an operating program group executable in the dental device.

3. Dental device according to claim 1 wherein the detection device (18) is provided with an image recognition device which is suitable for recognizing an image of the object (24) detected by the detection device and/or features of the image.

4. Dental device according to claim 1, wherein the data consists of at least one image and/or at least one parameter of the object (24).

5. Dental device according to claim 4, wherein the at least one parameter of the object (24) is a physical and/or optical feature of the object (24), comprising outer contour, height, width, surface condition, colors, patterns, and/or primer coat of the object.

6. Dental device according to claim 1, wherein the detection device (18) is provided with at least one camera (20) or at least one image sensor, wherein detection areas (22) extend into the interior of the dental device (10) and/or outside the dental device (10).

7. Dental device according to claim 1, wherein the detection device (18) detects the position and/or the rotational position of the object (24) in space and can be pivoted at the dental device (10) or relative to the dental device.

8. Dental device according to claim 1, wherein comparing the data of a detected object (24) with the data of the stored objects is realized using a comparison device.

9. Dental device according to claim 1, wherein data of at least two objects (24) is displayed on a display device (14), wherein the displayed data is most similar to the data of the detected object (24) and that the user himself/herself chooses the data which corresponds to the operating program or operating program group.

10. Dental device according to claim 9, wherein the display device (14) is suitable for displaying the object (24) detected by the detection device (18) reduced or increased in size.

11. Dental device according to claim 1, where an image recognition device is suitable for identifying an object (24) with the help of detected features of an image for starting the operating program associated with the object or for showing it for selection.

12. Dental device according to claim 1, wherein the dental device (10) is formed by a dental firing furnace or by a dental press furnace or by a light curing device.

13. Dental device according to any of the preceding claim 1, wherein the data is stored in a database with objects which have been stored in advance, which database is comparable with a central server via the Internet and carries out an automatic comparison when it is connected to the Internet.

14. Dental device according to claim 1, wherein the executable operating program or the executable operating program group is carried out upon confirmation by the user, by pressing a confirmation key, wherein in particular the key forms an indicator of confirmation.

15. Dental device according to claim 1, wherein in a plurality of dental devices which are configured as firing furnaces a subsidiary display or a central display is implemented in a control room, wherein the subsidiary or central display is switchable for several firing furnaces.

* * * * *